(12) United States Patent
Gehring (10) Patent No.: US 8,997,557 B2
(45) Date of Patent: Apr. 7, 2015

(54) DEVICE AND METHOD FOR CARRYING OUT MEASUREMENTS OF AN ANALYSIS FLUID

(75) Inventor: Frank Gehring, Obernheim (DE)

(73) Assignee: Andreas Hettich GmbH & Co. KG, Tuttlingen (DE)

( * ) Notice: Subject to any disclaimer, the term of this patent is extended or adjusted under 35 U.S.C. 154(b) by 1084 days.

(21) Appl. No.: 13/000,006

(22) PCT Filed: Jun. 19, 2009

(86) PCT No.: PCT/EP2009/004466
§ 371 (c)(1),
(2), (4) Date: May 19, 2011

(87) PCT Pub. No.: WO2009/153063
PCT Pub. Date: Dec. 23, 2009

(65) Prior Publication Data
US 2011/0283781 A1 Nov. 24, 2011

(30) Foreign Application Priority Data
Jun. 19, 2008 (DE) .......................... 10 2008 029 213

(51) Int. Cl.
*G01N 29/00* (2006.01)
*G01N 29/036* (2006.01)
*G01N 29/02* (2006.01)
*G01N 29/22* (2006.01)

(52) U.S. Cl.
CPC ............ *G01N 29/036* (2013.01); *G01N 29/022* (2013.01); *G01N 29/222* (2013.01); *G01N 2291/014* (2013.01); *G01N 2291/0255* (2013.01); *G01N 2291/0256* (2013.01)

(58) Field of Classification Search
CPC ..................... G01N 29/022; G01N 2015/0687
USPC ......................................... 73/64.53
See application file for complete search history.

(56) References Cited

U.S. PATENT DOCUMENTS

| 5,542,298 A | 8/1996 | Sarvazian et al. |
| 6,644,119 B1 | 11/2003 | Sinha |
| 2004/0019462 A1* | 1/2004 | Gehrlein et al. .............. 702/188 |
| 2007/0283748 A1 | 12/2007 | Funck et al. |
| 2009/0173158 A1* | 7/2009 | Gehring .......................... 73/590 |

FOREIGN PATENT DOCUMENTS

| DE | 10137679 C1 | 12/2002 |
| WO | 2004067130 A2 | 8/2004 |
| WO | 2007028820 A1 | 3/2007 |
| WO | 2007112897 A2 | 11/2007 |

OTHER PUBLICATIONS

Schultz, J. et al., A Continuous Wave Transmission Method for the Ultrasonic Spectrometry of Liquids, Measurement Science and Technology, IOP, Bristol, GB, vol. 9, No. 8, Aug. 1, 1998.

(Continued)

*Primary Examiner* — Laura Martin
*Assistant Examiner* — Alex Devito
(74) *Attorney, Agent, or Firm* — Woodling, Krost and Rust (57) ABSTRACT

The invention relates to an apparatus (10) for carrying out measurements of a analyte fluid having a housing (12, 18), a measurement chamber (40) arranged in the housing (18), a resonator (16, 34) and conduits (42, 44) for inputting and outputting media for the measurements into/out of the measurement chamber (40), wherein the resonators (16, 34) delimit the measurement chamber (40) in areas. The invention distinguishes thereby that two resonators (16, 34) are provided which delimit the measurements chamber (40) each.

2 Claims, 5 Drawing Sheets

(56) References Cited

OTHER PUBLICATIONS

International Search Report, PCT/EP2009/004466, Oct. 14, 2009.
European Patent Office, Office Action, Mar. 8, 2013, pp. 1-6, Patent Application No. 09765643.3, Applicant: Andreas Hettich GmbH & Co. KG, Munich, Germany.
German Patent and Trademark Office, German Examination Report Dated Jan. 21, 2009, German Serial No. 10 2008 029 213.3-52, Filed June 19, 2008, pp. 1-3, Munich, Germany.
German Patent and Trademark Office, German Examination Report Dated April 4, 2011, German Serial No. 10 2008 029 213.3-52, Filed June 19, 2008, pp. 1-4, Munich, Germany.
German Patent and Trademark Office, Office Action, German Application No. 102008029213.3, Applicant: Andreas Hettich GmbH & Co. KG, Jan. 9, 2014, pp. 1-4, Germany.
Dr. Marcus Preisinger, Translation of the German Office Action, Jan. 9, 2014, File No. 102008029213.3, pp. 1-3.

* cited by examiner

DEVICE AND METHOD FOR CARRYING OUT MEASUREMENTS OF AN ANALYSIS FLUID

The invention refers to an apparatus for carrying out measurements of an analyte fluid.

Such apparatuses for carrying out measurements of an analyte fluid are, for example, known from WO 2007/112897 A2. Therein, the apparatus consists out of a housing, a measurement chamber arranged in the housing, a resonator in form of an oscillating quartz, an upper part for delimiting the measurement chamber to the top and conduits for inputting and outputting of media for the measurements in the measurement chamber. In the measurement chamber, there is provided a resonator each which delimits the measurement chamber in its upper area. Therein, the resonator rests on a pedestal of the housing. On the side opposite to the pedestal of the housing, a sealing ring is arranged on which the upper part is resting.

The upper part is formed in the shape of a removable insert and is adapted to be locked to the housing by means of a bayonet fitting. The insert comprises an optical window in the center by which one can have an inside into the measurement chamber. The insert with the lens delimits the measurement chamber to the top and the sealing ring delimits the measurement chamber to the side. The sealing ring is, therein, fixatedly connected to the insert in order to allow for an easy exchange of the resonator.

The oscillating quartz which forms the resonator, is fixatedly and continuously connected with its side area with a foil ring which is again connected to a supporting ring radial further to the outside. The foil ring ensures the sealing of the measurement chamber as well as the oscillating movement of the oscillating quartz. The supporting ring provides a predefined arrangement in the housing.

With this known apparatus for carrying out measurements of an analyte fluid, measurement procedures can be realized in a simple manner which, up to now, where only possible with high complexity, for example methods for determining blood groups.

Furthermore, it is known from WO 2004/067130 A2, to carry out different measurements in analyte fluids, also blood, by means of a resonator which measurements go beyond the pure blood group determination. For determining of for example irregular antibodies and isoagglutinines, the expenditure is relatively high and requires still some handwork and also takes relative long time.

An apparatus for carrying out measurements of an analyte fluid is also known from the DE 101 37 679 C1, wherein the housing comprises a measurement chamber and two oppositely arranged resonators delimiting the measurement chamber in certain areas.

An apparatus for determining physical state parameters of a medium is disclosed in the U.S. Pat. No. 5,542,298. The apparatus comprises a hollow base body having an opening in its wall, converters of acoustic oscillations fixed to its front ends and provided with electrodes which form a measurement chamber together with the base body, and fixing elements. Each converter of acoustic oscillations is fixately attached in the parameter between the front end of the base body and a fixing element. The surface of each converter of acoustic oscillations contacting the medium to be studied, is formed as a unitary electrode coaxially with the measurement chamber and coincides therewith in diameter. Several measurement chambers may be arranged in the base body.

A method for a non invasive characterization of a flowing multiphase fluid using ultrasonic interferometry as well as an apparatus for carrying out the method is disclosed in the U.S. Pat. No. 6,644,119 B1.

From the publication "A continuous wave transmission method for the ultrasonic spectrometry of liquids", Measurement Science and Technology, 9, (1998), Pages 1266-1276, a further method for determining physical properties of liquids is known as well as an apparatus for carrying out the method.

Therefore, the invention is directed to the objective to provide an apparatus with which more possibilities for measurements are obtained and by which the above-mentioned deficiencies are avoided.

The invention is based on the finding that, by simultaneously providing two resonators, a plurality of measurements or a plurality of measurements in a time sequence can be carried out without changing in the parts which delimit the measurement chamber. Thereby, the expenditure for measurements can be considerably reduced, the speed of the measurements can be put up and the factors negatively influencing the measurements results can be minimized. Furthermore, also further measurement possibilities are obtained which where possible, up to now, only one after another, or with a lot of complexity.

According to the invention, in the apparatus for carrying out of measurements of an analyte fluid, two resonators are therefore provided which each delimit the measurement chamber wherein, with reference to the direction of gravity, the first resonator is arranged at the top in the housing and the second resonator is arranged opposite at the bottom in the housing. Herein, the first resonator is formed as an actuator and/or sensor, and the second resonator is formed as a sensor and/or actuator.

Because of the construction of the first resonator as actuator and/or sensor and the construction of the second resonator as sensor and/or actuator as well as because of the upper and lower arrangement of the sensors in the housing, it is assured in an advantageous way that, upon separating of an analyte from the upper first resonator, the analyte settles on the lower resonator by means of gravity. Now, the analyte can be subjected to further measurement method steps in the lower part with the aid of the lower resonator, and the upper resonator can carry out other measurement method steps, for example it can examine the matrix of the analyte fluid.

Preferably, the first and/or the second resonator are therein removably fixed to the measurement chamber. The removable construction has shown to be advantageous since a simple handling is assured thereby, in particular with respect to the cleaning of the resonators or the coating of the resonators. Furthermore, it is conceivable that, in place of a resonator, a acrylic glass is fixed to the measurement chamber. Thereby, an inspection of the measurement chamber is ensured.

According to the claimed embodiment, the two resonators delimit the measurement chamber each with a resonator surface facing the measurement chamber. Preferably, the surfaces of the two resonators facing the measurement chamber, comprise the same electrical potential. Thereby, an electrical coupling of the two resonators among others by means of an electrically conductive fluid is avoided.

This is particularly important when one of the two resonators is operated as an actuator with a very high alternating voltage.

According to a particularly preferred embodiment, the housing is arranged to be rotatable, in particular rotatable by 180 degrees. Thereby, combined measurement methods for transferring the analyte from the second resonator to the first resonator with the aid of gravity are made possible in a simple way.

In order to enable a secure arrangement of the resonators in the housing, they are abut each at a portion of the housing, in particular at a land of the housing. In particular, the land is arranged in parallel to the resonator completely circumferentially at the side of the measurement chamber. On the one hand, the resonators are thereby fixatedly arranged with respect to their spatial arrangement, on the other hand, further constructive possibilities are thereby given as will be shown in the following.

The housing may be constructed by a plurality of parts. It may consist out of a basic housing and a measurement chamber housing. The measurement chamber housing and the basic housing are, in particular removably, connected to each other.

From the WO 2007/112897 A2, resonators are known which comprise a supporting ring. Therein, the resonator is connected, at its periphery, to the supporting ring by means of a foil ring in order to form a resonator unit. The foil ring and the supporting ring form, together with the resonator, a sealing surface such that no fluid can pass from the one side of the resonator unit to the other side of the resonator unit. Such resonators in resonator units have proven of value. In so far, also the apparatus according to the present invention may comprise resonator units constructed according to the WO 2007/112897 A2. Therein, the resonators are supported in a support radially surrounding the resonator.

The support comprises, therein, the supporting ring as well as the foil ring. Therein, a sealing means is arranged in particular between the supports of the resonators, in particular in between each support and the land of the housing. With this sealing means, it is intended to avoid that medium can exit the measurement chamber for example between the supporting ring and the land of the housing. Thereby, the result of the measurement would be tampered.

In a simple way, the sealing means may be applied in form of a layer on the support, in particular on the foil ring. Preferably, the layer is therein formed by silicon, in particular by polydimethylsiloxane—PDMS.

In order to input and output the analyte fluid into/out of the measurement chamber, on the one hand, but also in order to carry out rinsing operations during or after the measurement or in order to input and output reagents, conduits are provided through the area of the housing to which the resonator units are abutting, in particular with their supporting rings.

In order to ensure a secure arrangement of the first resonator in the housing, a locking mechanism is installed which secures the first resonator in the housing.

The invention also refers to a method for measuring the physical parameters of the analyte fluid and/or at least of one analyte and/or the matrix of the analyte fluid with an apparatus as described above.

According to a first embodiment, the method comprises the following method steps:
  a. Outside of the measurement chamber, carrier particles are immobilized on the resonator surface of one of the two resonators (34, 16);
  b. The resonator (34, 16) is connected to the measurement chamber (40) in such a way that the resonator surface immobilized with the carrier particles, is reaching into the measurement chamber;
  c. The analyte fluid is input into the measurement chamber (40) such that parts of the analyte fluid are attached to the resonator surface of the resonator;
  d. The measurement chamber (40) is rinsed in order to remove residual constituents of the analyte fluid from the measurement chamber (40);
  e. The arrangement is now, if necessary by a rotation of about 180°, adjusted such that the resonator with the attached carrier particles is arranged with respect to the direction of gravity at the top in the housing;
  f. The resonator (34, 16) which is arranged at the top of the housing with respect to the direction of gravity, is now stimulated with a very high amplitude of oscillation in order to separate the carrier particles arranged at the resonator surface and the parts of the analyte fluid attached thereto;
  g. The carrier particles and the parts of the analyte fluid attached thereto fall, because of gravity, onto the resonator (16, 34) which is arranged at the bottom of the housing with reference to gravity, and they are attached up there to the surface of the resonator (16, 34) facing the measurement chamber (40), in particular by means of specific captor molecules;
  h. The resonator arranged at the bottom with respect to the direction of gravity, is put into oscillation, and the mass distribution is determined.

According to a further embodiment, the method comprises the following method steps.
  a. Within the measurement chamber, the resonator surface of the resonator which is arranged at the bottom of the housing with respect to the direction of gravity, is pre-coated with captor molecules;
  b. At the resonator surface which is pre-coated with captor molecules, carrier particles are immobilized;
  c. The analyte fluid is input into the measurement chamber (40) such that parts of the analyte fluid are attached to the resonator surface of the resonator which is arranged at the bottom of the housing as seen in the direction of gravity;
  d. The measurement chamber (40) is rinsed in order to remove residual constituents of the analyte fluid out of the measurement chamber (40);
  e. The arrangement is now adjusted by rotation about 180 such that the resonator with the attached carrier particles is arranged at the top of the housing with respect to the direction of gravity;
  f. The resonator (34, 16) arranged at the top of the housing with respect to the direction of gravity, is now stimulated with a very high oscillation amplitude in order to separate the carrier particles arranged at the surface, and the parts of the analyte fluid attached thereto;
  g. The carrier particles and the parts of the analyte fluid attached thereto fall, because of gravity, onto the resonator (16, 34) arranged at the bottom in the housing with respect to gravity, and are there attached to the surface of the resonator (16, 34) facing the measurement chamber (40) in particular by means of specific captor molecules;
  h. The resonator arranged at the bottom with respect to the direction of gravity, is put into oscillation, and the mass distribution is determined.

As is known, the frequency signal or the impedance signal, respectively, of resonators is composed out of two different influence values. On the one hand, a change in a signal is effected on the basis of changes in the physical parameters of the fluid (frequency change); and is proportional to the root out of product (density of the fluid*viscosity of the fluid). On the other hand, the frequency change is proportional to the attached mass at the resonator surface. Because of the inventive arrangement of the two resonators, now the combination of the signals of both resonators in one measurement method is possible in an advantageous way, i.e. it is possible to separate both effects and to make accurate statements on the physical properties of the fluid and the attached impurity layer.

Further advantages, features and application possibilities of the present invention can be taken from the following description in connection with the embodiments shown in the drawings.

The invention is described in the following in more detail with reference to the embodiments shown in the drawings. In the specification, in the patent claims and in the abstract and in the drawings the terms and related reference signs are used as listed in the list of reference signs given below. In the drawings:

Figure 1:
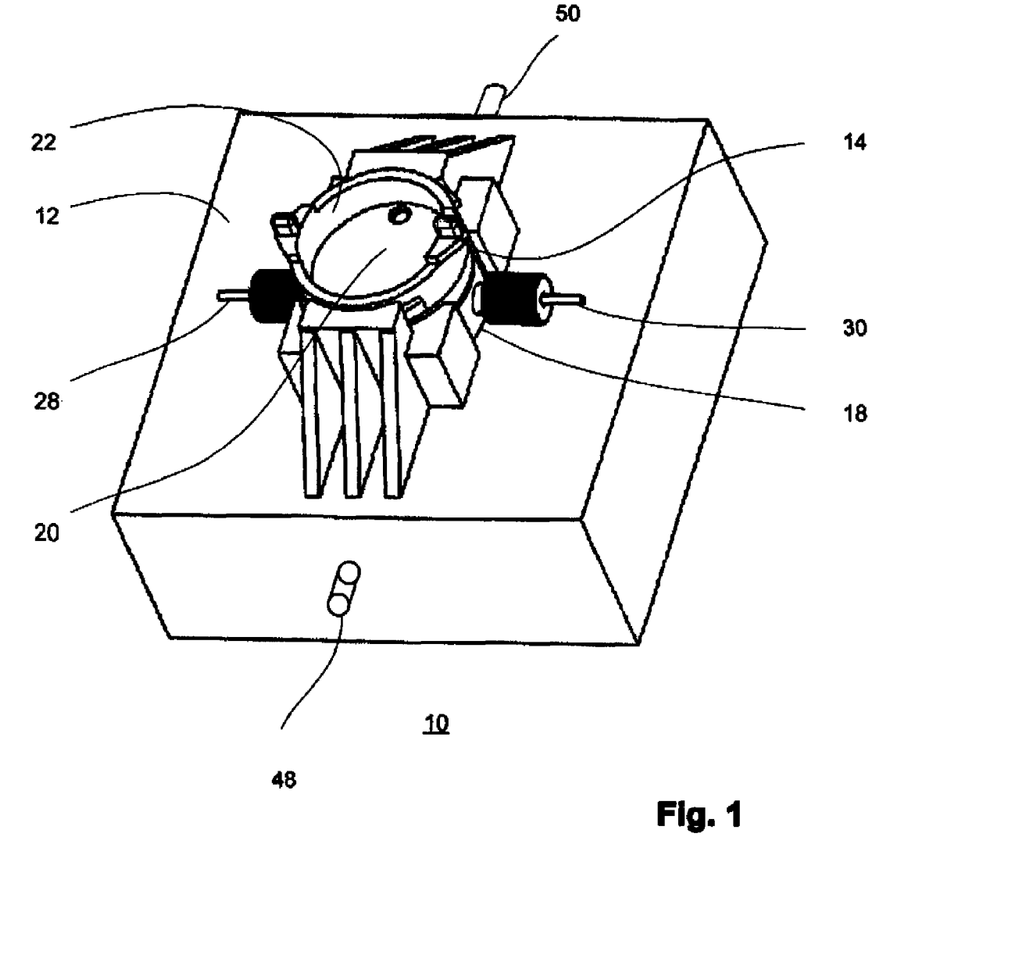
FIG. 1 is a perspective view on the apparatus according to the invention.
Figure 2:
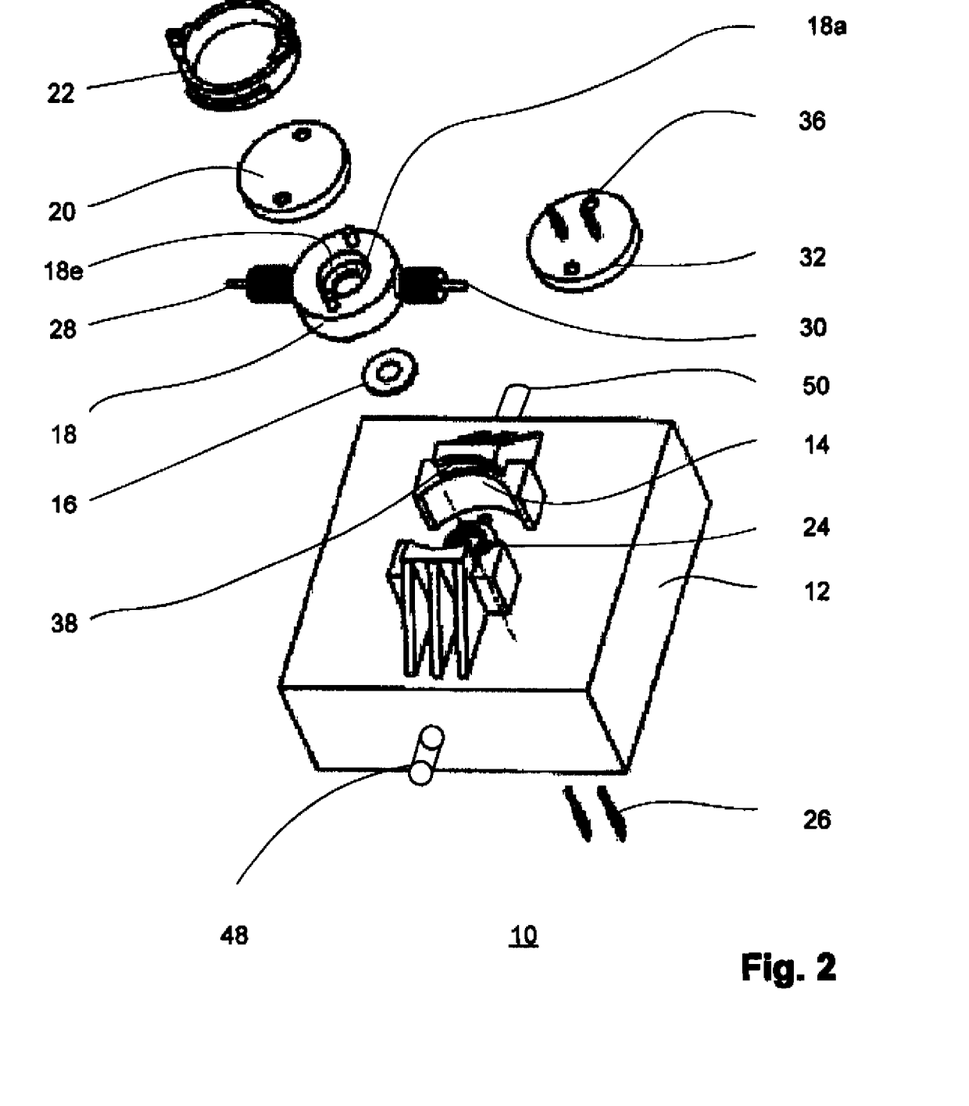
FIG. 2 is an exploded view of the apparatus with a resonator unit and an insert of FIG. 1.
Figure 3:
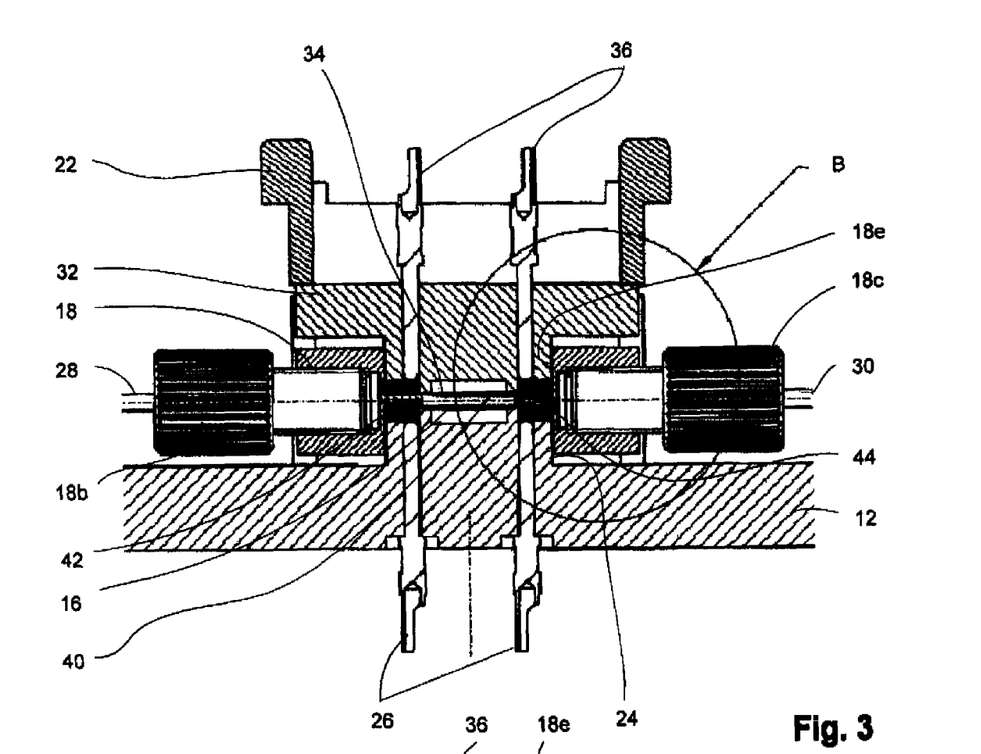
FIG. 3 is a section view through the housing of FIG. 1 and using two oppositely arranged resonator units.
Figure 4:
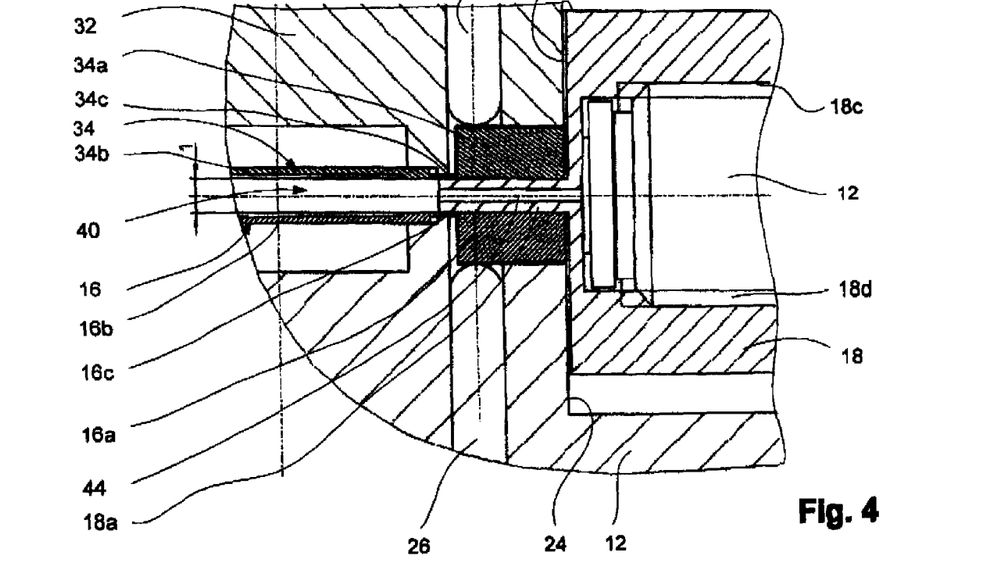
FIG. 4 is an enlarged detail view of FIG. 3 where the enlarged area is designated there by A.
Figure 5:
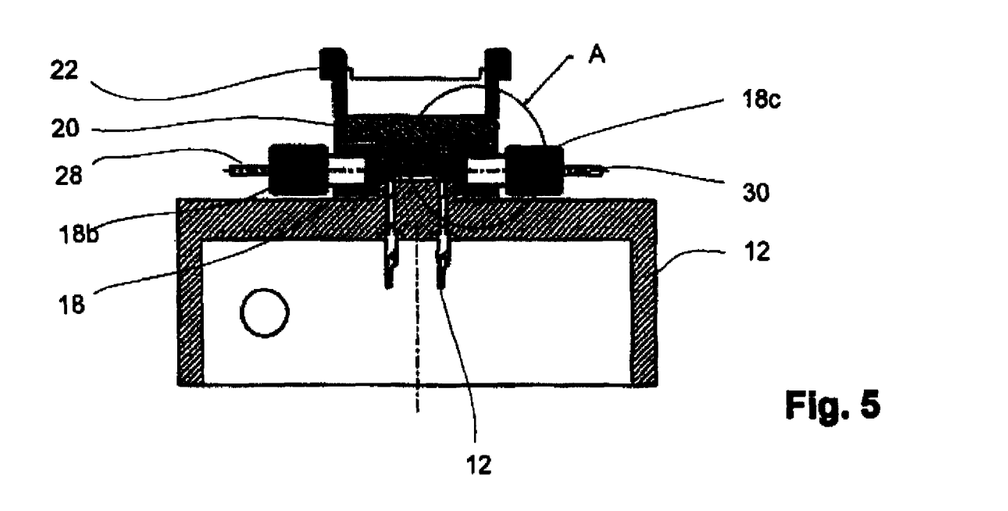
FIG. 5 is a sectional view with a resonator unit and an insert.
Figure 6:
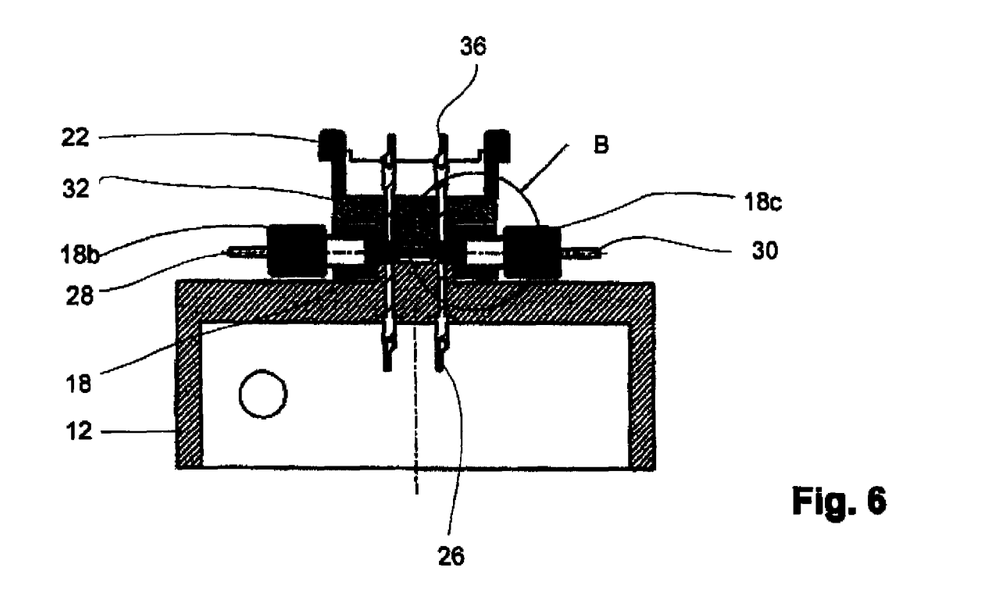
FIG. 6 is a sectional view of the apparatus with two resonator units.
Figure 7:
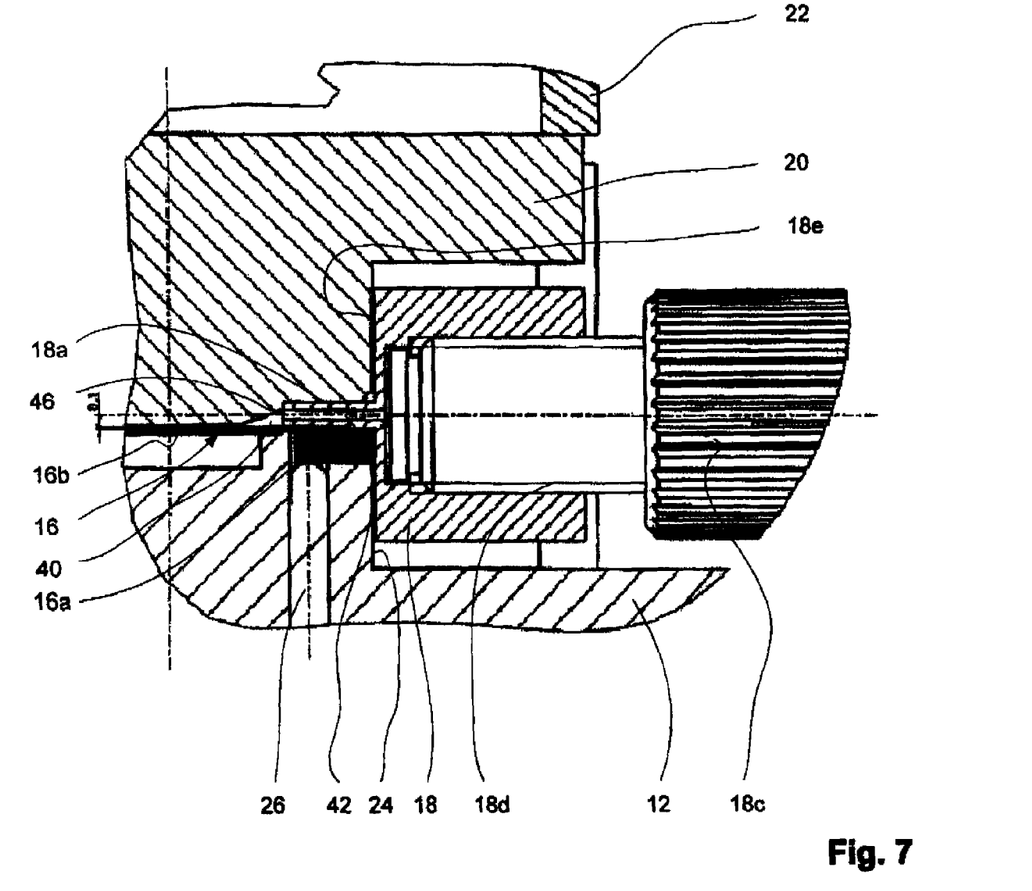
FIG. 7 is an enlarged sectional view of FIG. 5 where the enlarged area is designated there with B.

In the FIGS. 1 to 7, an embodiment of an apparatus 10 for carrying out of measurements of analyte fluid is shown. The apparatus 10 comprises a basic housing 12 with a receptacle 14 arranged on top of the basic housing 12. The receptacle 14 serves for receiving a second oscillating quartz unit 16, a measurement chamber housing 18, a first oscillating quartz unit 34 as well as a closure ring 22.

A protrusion 24 for the second oscillating quartz unit 16 is arranged on the basic housing 12 in the receptacle 14. The protrusion 24 serves for positioning and for electrical contacting the oscillating quartz unit 16 by means of two contact surfaces. The contact surfaces are, therein, electrically connected to the contact pins 26. Thereby, the electrical voltage can be applied to the oscillating quartz 16b in a simple way. The contact pins 26 are, for this purpose, connected to a voltages source which is not shown here.

The protrusion 24 is adapted to the outer shape of the oscillating quartz unit 16 with respect to the radial extension and shaping.

The measurement chamber housing 18 is put onto the oscillating quartz unit 16 which is put onto the protrusion 24. The measurement chamber housing 18 is provided with a bore 18e into which a land 18a protrudes centrally and annularly. Therein, the measurement chamber housing 18 abuts with its and 18a to the oscillating quartz unit 16.

The measurement chamber housing 18 is provided with two connectors 18b, 18c at which the conduits 28 and 30, respectively, are ending. The connectors 18b, 18c are screwed into the measurement chamber housing 18 and are removably arranged there by means of a thread connection 18d.

The second oscillating quartz unit 16 consists out of a supporting ring 16a and of a ring foil 16c connecting the supporting ring 16a and the oscillating quartz 16b. The supporting ring 16a, the ring foil 16c and the oscillating quartz 16b together form a sealed surface through which no medium can penetrate.

The supporting ring 16a is located, in its mounted state, on the protrusion 24 of the basic housing 12. On the opposite side, the land 18a of the measurement chamber housing 18 rests on the supporting ring 16a. A further, first oscillating quartz unit 34 rests again on the land 18a and is, thereby, electrically connected to the contact pins 36.

The first oscillating quartz unit 34 consists out of a supporting ring 34a and a ring foil 34c connecting the supporting ring 34a and the oscillating quartz 34b. The supporting ring 34a, the ring foil 34c and the oscillating quartz 34b together form a sealed surface through which no medium can penetrate.

This first oscillating quartz 34 is pressed, in its mounted state, by the holder 32 against the and 18a of the measurement chamber housing 18. The holder 32 is engaged by the closure ring 22 which, by means of a bayonet fitting 38, with the receptacle 14 in the direction of the basic housing 12 puts under tension the first oscillating quartz insert 34 with the holder 32 of the measurement chamber housing 18, the second oscillating quartz 16 against the protrusion 24 in the receptacle 14 of the housing 12.

The holder 32 serves for the positioning and the electrical contacting of the oscillating quartz unit 34 through contact surfaces. The contact surfaces are, therein, electrically connected to the contact pins 36. In this way, the electrical voltage can, thereby, be applied to the oscillating quartz 34b. The contact pins 36 are, for this purpose, connected to an electrical voltage source which is not shown here. Thereby, the electrical voltage can be applied to the oscillating quartz 34 in a simple way.

The oscillating quartz units 16 and 34 delimit the measurement chamber 40 each to the top and to the bottom. The measurement chamber 40 is delimited to the side by the land 18a. In order to enable a sealed arrangement between the oscillating quartz units 16, 34 and the land 18a, the oscillating quartz units 16, 34 are covered, at least in the area of their supporting rings 16a, 34a, with a sealing layer, for example out of silicone, in particular out of polydimethylsiloxane PDMS.

As already explained above, the conduits 28, 30 are connected through connectors 18b, 18c to the measurement chamber housing. The connectors 18b, 18c are connected through conduits 42 and 44 to there conduits 28, 30 with the measurement chamber 40. Thereby, at the one hand, the analyte fluid may be input and output into/out of the measurement chamber, but also rinsing during or after the measurement may be carried out, reagents may be input and output.

The basic housing 12 is arranged in a suspension which is not shown here in detail. In this suspension, the basic housing 12 may be rotated, in particular about 180°. For the purpose of the suspension, pivot pins 48 and 50 are formed at the side of the basic housing 12. The rotation is effected by means of a motor which cooperates with a control device.

By means of the inventive apparatus 10, it is now possible to carry out the following methods for measuring the physical parameters of the analyte fluid and/or at least one analyte and/or the matrix of the analyte fluid.

Therein, the method may comprise the following method steps:

a. Outside of the measurement chamber, carrier particles are immobilized on the resonator surface of one of the two resonators (34, 16);

b. The resonator (34, 16) is connected to the measurement chamber (40) in such a way that the resonator surface immobilized with the carrier particles, is reaching into the measurement chamber;

c. The analyte fluid is input into the measurement chamber (40) such that parts of the analyte fluid are attached to the resonator surface of the resonator;

d. The measurement chamber (40) is rinsed in order to remove residual constituents of the analyte fluid from the measurement chamber (40);
e. The arrangement is now, if necessary by a rotation of about 180°, adjusted such that the resonator with the attached carrier particles is arranged with respect to the direction of gravity at the top in the housing;
f. The resonator (34, 16) which is arranged at the top of the housing with respect to the direction of gravity, is now stimulated with a very high amplitude of oscillation in order to separate the carrier particles arranged at the resonator surface and the parts of the analyte fluid attached thereto;
g. The carrier particles and the parts of the analyte fluid attached thereto fall, because of gravity, onto the resonator (16, 34) which is arranged at the bottom of the housing with reference to gravity, and they are attached up there to the surface of the resonator (16, 34) facing the measurement chamber (40), in particular by means of specific captor molecules;
h. The resonator arranged at the bottom with respect to the direction of gravity, is put into oscillation, and the mass distribution is determined.

It is also conceivable that the method comprises the following method steps.
a. Within the measurement chamber, the resonator surface of the resonator which is arranged at the bottom of the housing with respect to the direction of gravity, is pre-coated with captor molecules;
b. At the resonator surface which is pre-coated with captor molecules, carrier particles are immobilized;
c. The analyte fluid is input into the measurement chamber (40) such that parts of the analyte fluid are attached to the resonator surface of the resonator which is arranged at the bottom of the housing as seen in the direction of gravity;
d. The measurement chamber (40) is rinsed in order to remove residual constituents of the analyte fluid out of the measurement chamber (40);
e. The arrangement is now adjusted by rotation about 180° such that the resonator with the attached carrier particles is arranged at the top of the housing with respect to the direction of gravity;
f. The resonator (34, 16) arranged at the top of the housing with respect to the direction of gravity, is now stimulated with a very high oscillation amplitude in order to separate the carrier particles arranged at the surface, and the parts of the analyte fluid attached thereto;
g. The carrier particles and the parts of the analyte fluid attached thereto fall, because of gravity, onto the resonator (16, 34) arranged at the bottom in the housing with respect to gravity, and are there attached to the surface of the resonator (16, 34) facing the measurement chamber (40) in particular by means of specific captor molecules;
h. The resonator arranged at the bottom with respect to the direction of gravity, is put into oscillation, and the mass distribution is determined.

LIST OF REFERENCE SIGNS a. apparatus
12 basic housing
14 receptacle
16 second oscillating quartz unit
16*a* supporting ring
16*b* quartz
16*c* ring foil
18 measurement chamber housing
18*a* and
18*b* connector, left
18*c* connector, right
18*d* threaded connection
18*e* bore in the measurement chamber housing
20 acrylic glass insert
22 closure ring
24 protrusion
26 contact pins
28 conduit—left
30 conduit—right
32 holder
34 first oscillating quartz unit
34*a* supporting ring
34*b* quartz
34*c* ring foil
36 contact pins
38 bayonet fitting
40 measurement chamber
42 conduit—left
44 conduit—right
46 oblique portion in the border area of the acrylic glass insert
48 pivot pin—left
50 pivot pin—right

The invention claimed is:

1. Method for measuring the physical properties of at least one analyte fluid and/or the matrix of said analyte fluid, comprising the following steps:
   utilizing one oscillating quartz unit and another oscillating quartz unit, said one oscillating quartz unit includes one surface and said another oscillating quartz unit includes a another surface;
   outside of a measurement chamber, carrier particles are immobilized on said one surface of said one oscillating quartz unit;
   said one oscillating quartz unit is connected to said measurement chamber such that said one surface of said one oscillating quartz unit is immobilized with said carrier particles and reaches into said measurement chamber;
   said at least one analyte fluid is input into said measurement chamber such that parts of said analyte fluid are attached to said one surface of said one oscillating quartz unit;
   said one oscillating quartz unit with said carrier particles attached to said one surface is rotatable 180°, if necessary, such that said one surface faces toward the earth in the direction of the gravitational attraction of said earth;
   said one oscillating quartz unit stimulated with a high amplitude of oscillation to separate said carrier particles and said parts of said analyte fluid attached to said one surface of said one oscillating quartz unit from said one surface of said one oscillating quartz unit;
   some of said carrier particles and said parts of said analyte fluid attached to said one surface of said one oscillating quartz unit fall under said gravitational attraction of said earth onto said another surface of said another oscillating quartz unit, some of said carrier particles and said parts of said analyte fluid remain attached to said one surface of said one oscillating quartz unit by means of specific captor molecules; and,
   said another oscillating quartz unit is oscillated and the mass distribution is determined.

2. Method for measuring the physical properties of at least one analyte fluid and/or the matrix of the analyte fluid, comprising the following steps:

utilizing one oscillating quartz unit and another oscillating quartz unit, said one oscillating quartz unit includes one surface and said another oscillating quartz unit includes a another surface;

within a measurement chamber, said one surface of said one oscillating quartz unit is pre-coated with captor molecules;

said analyte fluid is input into said measurement chamber such that parts of said analyte fluid are attached to said one surface of said one oscillating quartz unit;

said one surface of said one oscillating quartz unit with said attached carrier particles is adjusted by rotation about 180° such that said one surface faces toward the earth in the direction of the gravitational attraction of said earth;

said one oscillating quartz unit stimulated with a high oscillation amplitude to separate some of said carrier particles and said parts of said analyte fluid attached to said one surface of said oscillating quartz from said one surface of said one oscillating quartz unit;

some of said carrier particles and said parts of said analyte fluid attached to said one surface of said one oscillating quartz unit fall under gravitational attraction of said earth onto said another surface of said another oscillating quartz unit, some of said carrier particles and said parts of said analyte fluid remain attached to said one surface of said one oscillating quartz unit by means of specific captor molecules; and,     said another oscillating quartz unit arranged is oscillated and the mass distribution is determined.

\* \* \* \* \*